(12) United States Patent
Bojarski et al.

(10) Patent No.: US 7,662,160 B2
(45) Date of Patent: Feb. 16, 2010

(54) SUTURE LOADING

(75) Inventors: Ray Bojarski, Attleboro, MA (US); George Sikora, Bridgewater, MA (US)

(73) Assignee: Smith & Nephew, Inc., Memphis, TN (US)

( * ) Notice: Subject to any disclaimer, the term of this patent is extended or adjusted under 35 U.S.C. 154(b) by 613 days.

(21) Appl. No.: 10/765,214

(22) Filed: Jan. 28, 2004

(65) Prior Publication Data

US 2005/0165416 A1    Jul. 28, 2005

(51) Int. Cl.
*A61B 17/04*    (2006.01)

(52) U.S. Cl. .................................................... 606/148

(58) Field of Classification Search ................ 606/146, 606/144, 148, 149, 232; 141/331; 446/220, 446/222; 33/726

See application file for complete search history.

(56) References Cited

U.S. PATENT DOCUMENTS

| | | | | |
|---|---|---|---|---|
| 2,882,645 | A | * | 4/1959 | Stivers ........................ 446/220 |
| 3,392,894 | A | * | 7/1968 | Standefer ..................... 226/89 |
| 3,752,516 | A | | 8/1973 | Mumma |
| 3,879,147 | A | * | 4/1975 | Morell ........................ 403/369 |
| 4,145,838 | A | * | 3/1979 | Mason ........................ 446/220 |
| 4,384,167 | A | | 5/1983 | Nestor |
| 4,385,575 | A | * | 5/1983 | Weber ......................... 112/224 |
| 4,615,532 | A | * | 10/1986 | Biller et al. ................... 279/32 |
| 4,715,841 | A | * | 12/1987 | Nelson et al. ................ 446/220 |
| 4,798,554 | A | * | 1/1989 | Nelson et al. ................ 446/220 |
| 5,290,247 | A | * | 3/1994 | Crittenden ................... 604/171 |
| 5,342,369 | A | | 8/1994 | Harryman, II |
| 5,423,837 | A | * | 6/1995 | Mericle et al. ............... 606/148 |
| 5,474,562 | A | * | 12/1995 | Orchowski et al. ........... 606/107 |
| 5,741,277 | A | | 4/1998 | Gordon et al. |
| 5,871,490 | A | | 2/1999 | Schulze |
| 5,895,395 | A | | 4/1999 | Yeung |
| 5,948,002 | A | * | 9/1999 | Bonutti ....................... 606/232 |
| 6,010,525 | A | * | 1/2000 | Bonutti et al. ............... 606/232 |

(Continued)

FOREIGN PATENT DOCUMENTS

EP    0776640 A2    6/1997

(Continued)

OTHER PUBLICATIONS

International Search Report (3 pages), for PCT/US2005/02346, mailed Jun. 21, 2005.

(Continued)

*Primary Examiner*—Julian W Woo
(74) *Attorney, Agent, or Firm*—Fish & Richardson P.C.

(57) ABSTRACT

A device includes a body defining a tapered hole for guiding a member, such as a suture thread, into a tube, and a slot communicating with the hole for separating the body and the member. The body defines a bore for receiving the tube. The bore communicates with the tapered hole. The bore has a constant diameter or is tapered. A width of the bore is greater than a width of a narrowest portion of the tapered hole. The slot extends from the tapered hole and the bore to an external surface of the body. A method includes coupling a body to an end of a tube, guiding a member into the tube through a tapered hole, and separating the body and the member by passing the member through a slot.

27 Claims, 6 Drawing Sheets

U.S. PATENT DOCUMENTS

| | | | |
|---|---|---|---|
| 6,152,944 A | 11/2000 | Holman et al. | |
| 6,224,586 B1 | 5/2001 | Stephens | |
| 6,375,534 B1* | 4/2002 | Burns | 446/220 |
| 6,416,529 B1 | 7/2002 | Holman et al. | |
| 6,430,804 B1* | 8/2002 | Nelson et al. | 446/222 |
| 6,449,865 B1* | 9/2002 | Heckman | 33/726 |
| 6,575,806 B1* | 6/2003 | Nelson et al. | 446/220 |
| 6,879,854 B2* | 4/2005 | Windheuser et al. | 600/434 |
| 6,916,014 B1 | 7/2005 | Thomas | |
| 2005/0154441 A1 | 7/2005 | Schaeffer et al. | |

FOREIGN PATENT DOCUMENTS

| | | |
|---|---|---|
| EP | 0812572 A1 | 12/1997 |
| WO | WO 01/35833 | 5/2001 |

OTHER PUBLICATIONS

Notification of Transmittal of the International Preliminary Report on Patentability, Serial No. PCT/US2005/002346, dated Jan. 26, 2006.

* cited by examiner

SUTURE LOADING

TECHNICAL FIELD

This invention relates to suture loading.

BACKGROUND

Suture threads are used in various techniques for tissue repair. Various types of suture pushers are used to guide and insert suture threads into tissue, especially in arthroscopic surgery. When using a suture pusher, a suture thread is threaded through an opening or window in the suture pusher, much like threading a needle when sewing.

SUMMARY

According to one aspect of the invention, a device includes a body defining a tapered hole for guiding a member, such as a suture thread, into a tube. The body also defines a slot communicating with the hole for separating the body and the member.

Embodiments of this aspect may include one or more of the following features. The body defines a bore for receiving the tube. The bore communicates with the tapered hole. The bore has, e.g., a constant diameter or is tapered. A width of the bore is greater than a width of a narrowest portion of the tapered hole. The slot extends from the tapered hole and the bore to an external surface of the body. A handle extends from the body.

According to another aspect of the invention, a device includes a tube and a body defining a tapered hole for guiding a member, such as a suture thread, into the tube. The body also defines a slot communicating with the hole for separating the body and the member.

Embodiments of this aspect may include one or more of the following features. The body is configured for connection to an end of the tube. The body defines a bore communicating with the tapered hole for receiving the tube. The bore has, e.g., a constant diameter or is tapered. A width of the bore is greater than a width of a narrowest portion of the tapered hole. The slot extends from the tapered hole and the bore to an external surface of the body. The tube defines an opening for receiving the member. A width of the opening is substantially the same as a width of the narrowest portion of the tapered hole. A handle extends from the body.

According to another aspect of the invention, a method includes coupling a body to an end of a tube. The body defines a tapered hole and a slot. The method includes guiding a member into the tube through the tapered hole, and separating the body and the member by passing the member through the slot. In an embodiment of this aspect, coupling includes receiving the end of the tube in a bore in the body. The bore communicates with the tapered hole.

According to another aspect of the invention, a device includes guide means for guiding a member into a tube. The guide means includes means for separating the guide means and the member. The guide means is, for example, is a tapered hole in a body. The means for separating is, for example, a slot in the body.

Advantages of the invention include, e.g., facilitating the threading of suture thread into an opening in a tube, and avoiding fraying of suture during insertion into the tube. Also, due to the ease of insertion, operating time during surgery can be reduced.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
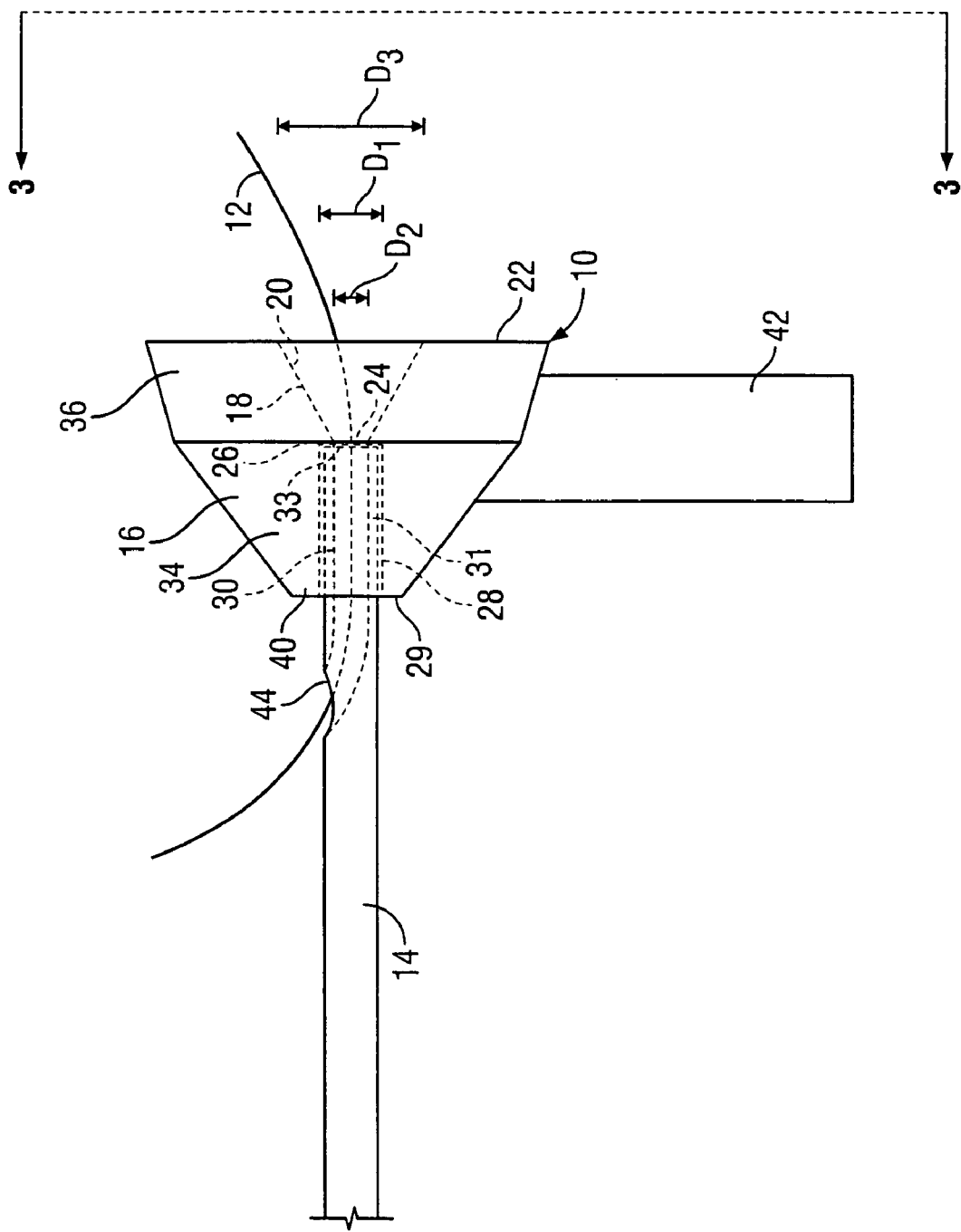
FIG. 1 is a side view of a suture loader being used to insert a suture thread into a tube.

Referring to FIG. 1, a suture loader 10 for use in threading a member, e.g., a suture thread 12, into a tube 14 includes a body 16 defining a tapered hole 18. Hole 18 tapers from a larger diameter opening 20 at a top surface 22 of suture loader 10, to a smaller diameter opening 24 at an internal region 26 of suture loader 10. Larger diameter opening 20 facilitates the threading of suture thread 12 into tapered hole 18. Suture loader 10 further defines a bore 28 extending from a bottom surface 29 of suture loader 10 to internal region 26 for communication with hole 18. Bore 28 is sized to receive tube 14 such that an opening 30 in an end portion 31 of tube 14 is aligned with smaller diameter opening 24 of hole 18 to receive suture thread 12 from hole 18. Bore 28 has a substantially constant diameter or tapers from a wider portion at bottom surface 29 to a narrower portion at internal region 26, for reasons discussed below.

Figure 2:
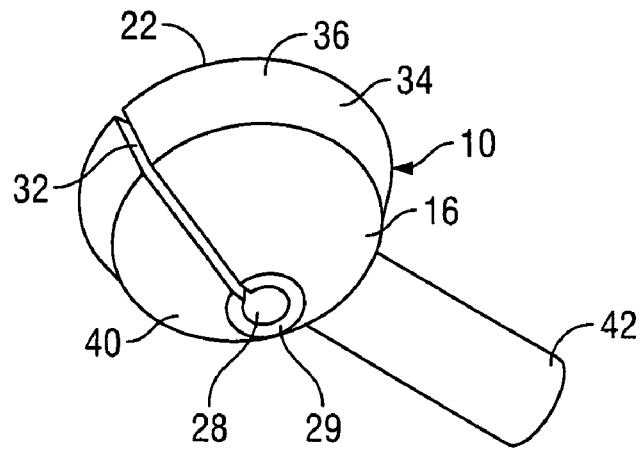
FIG. 2 is a perspective view of the suture loader of FIG. 1.

Referring to FIG. 2, body 14 also defines a slot 32 communicating with tapered hole 18 and bore 28. Slot 32 extends from tapered hole 18 and bore 28 to an external surface 34 of suture loader 14 and to top and bottom surfaces 22, 29. Slot 32 allows the user to separate body 16 and suture thread 12, after suture thread 12 has been threaded through tapered hole 18 and into opening 30 in tube 14, by passing suture thread 12 through slot 32 and out of body 16.

Referring again to FIG. 1, to receive tube 14 in bore 28, a diameter $D_1$ of bore 28 is slightly greater than an outer diameter of tube 14. To facilitate inserting suture thread 12 through opening 30 in tube 14, a diameter $D_2$ of opening 24 is approximately the same as or slightly greater than a diameter of an entry hole 33 of opening 30 in tube 14. Thus, diameter $D_1$ of bore 28 is greater than diameter $D_2$ of opening 24. As previously discussed, diameter $D_3$ of opening 20 is larger than diameter $D_2$ of opening 24. For example, for a tube 14 having an outer diameter of approximately 0.0625 inches, and a diameter of entry hole 33 of 0.023 to 0.025 inches, diameter $D_1$ of bore 28 is approximately 0.063 to 0.065 inches, diameter $D_2$ is approximately 0.027 to 0.030 inches, and diameter $D_3$ is approximately 0.120 to 0.130 inches. Alternatively, bore 28 can taper to a smaller diameter at internal region 26 that is smaller than the diameter of tube 14, e.g., by about 0.003 inches, such that there is a slight friction fit between tube 14 and bore 28, which helps to keep suture loader 10 on tube 14 during threading of suture thread 12, and which allows suture loader 10 to be subsequently removed from tube 14.

Figure 3:
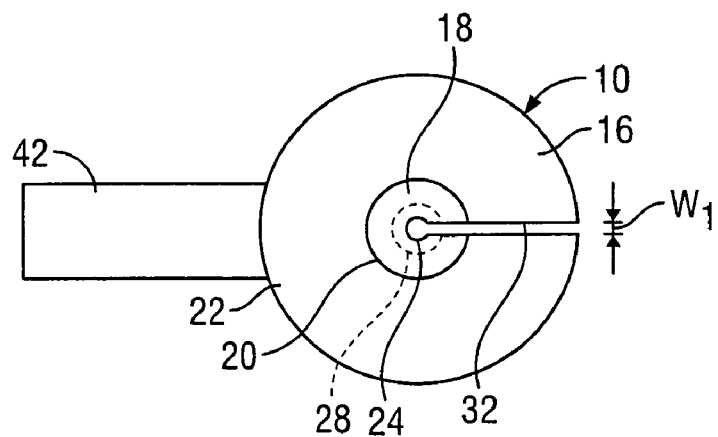
FIG. 3 is a front view of the suture loader of FIG. 1, taken along lines 3-3 in FIG. 1.

Referring to FIG. 3, slot 32 has a width $W_1$ slightly smaller than diameter $D_2$ of opening 24, but slightly larger than a width of suture thread 12. Width $W_1$ is selected such that the user can thread suture thread 12 through tapered hole 18 without suture thread 12 unintentionally slipping out of slot 32 and can remove suture thread 12 through slot 32 once suture thread 12 has been inserted into opening 30 in tube 14. For example, for a diameter $D_2$ of 0.027 to 0.030 inches and a suture thread width of 0.011 to 0.013 inches (size 0 suture thread), width $W_1$ can be approximately 0.012 to 0.020 inches.

Referring again to FIGS. 1 and 2, extending from body 14 is a substantially cylindrical handle 42 that allows the user to hold suture loader 10 in one hand while inserting suture thread 12 into suture loader 10 with the other hand. Handle 42 is oriented opposite of slot 32 to provide the user a visual and tactile reference as to the orientation of slot 32. External surface 34 of suture loader 10 includes a portion 36 that tapers from a larger width at top surface 20 to an intermediate width at internal region 26, and a bottom portion 40 that tapers from the intermediate width to a smaller width at bottom surface 29.

Suture receiving opening 30 in tube 14 extends from end portion 31 of tube 14 to a side port 44. An example of tube 14 in the form of a suture pusher is described in co-pending U.S. patent application Ser. No. 10/370,276, the entirety of which is incorporated herein by reference.

Figure 4:
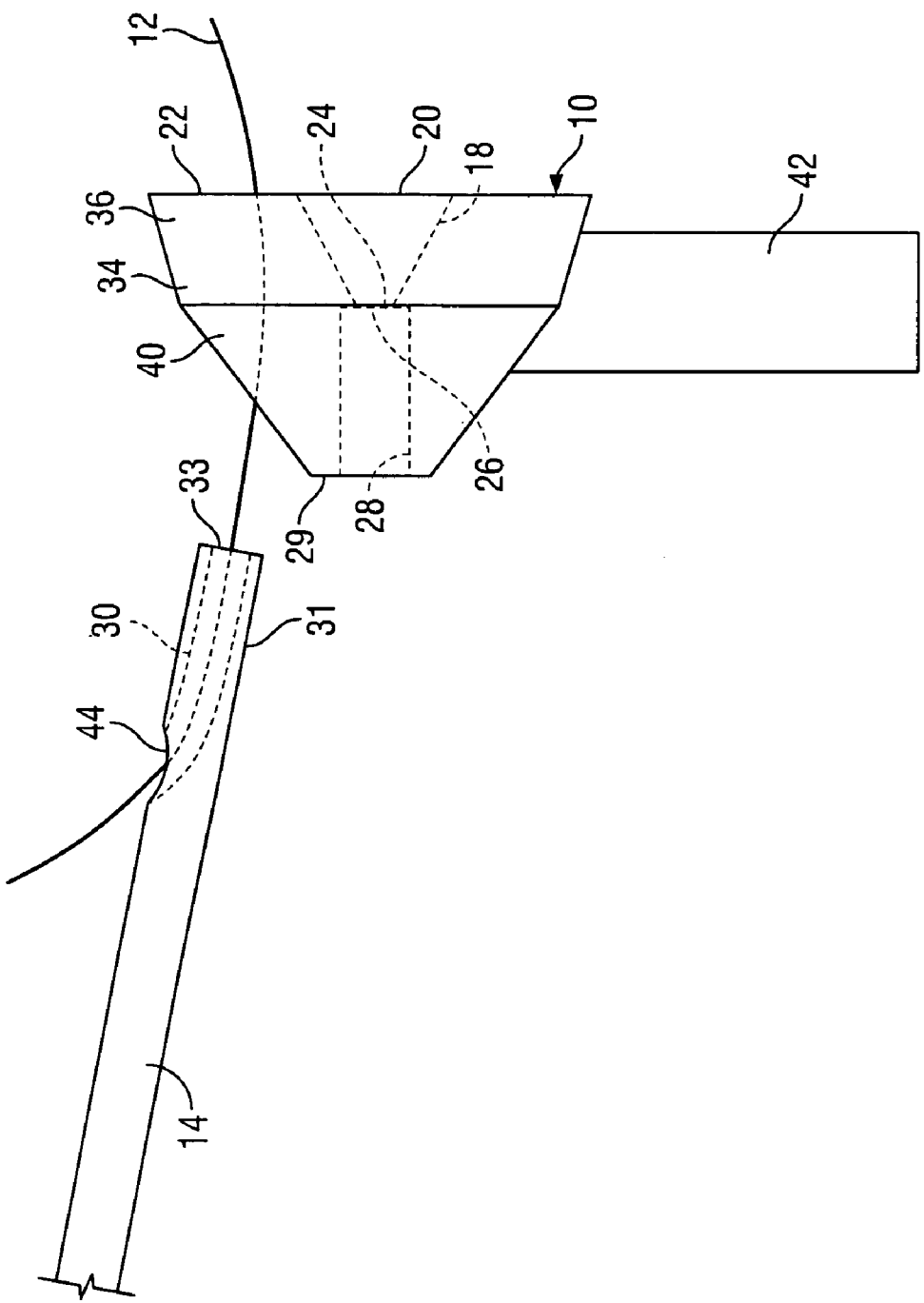
FIG. 4 is a side view of the suture loader of FIG. 1 showing the suture thread and the suture loader being separated.

Referring to FIGS. 1 and 4, in use, suture loader 10 is coupled to end portion 31 of tube 14 by inserting end portion 31 into bore 28, so that end portion 31 abuts internal region 26 around opening 24 and opening 30 is aligned with opening 24. Suture thread 12 is inserted into tapered hole 18 through opening 20 and guided through tapered hole 18 and into entry hole 33 of tube 14. Suture thread 12 is advanced through opening 30 and out port 44. Next, tube 14 is removed from bore 28 and suture thread 12 is separated from body 16 by passing suture thread 12 through slot 32, as shown in FIG. 4.

Figure 5:
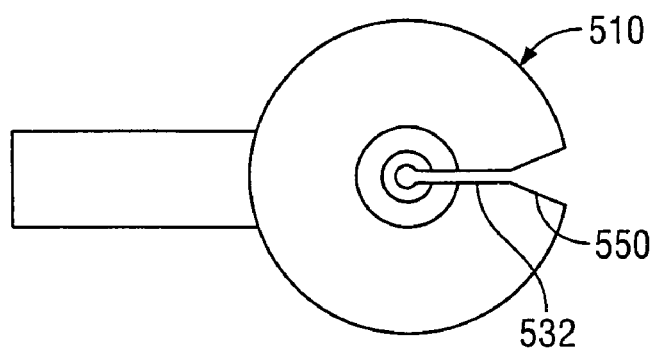
FIG. 5 is a front view of a second embodiment of a suture loader.

Referring to FIG. 5, an alternative suture loader 510 has a slot 532 for separating suture thread 12 and suture loader 510. Suture loader 510 includes a tapered portion 550 that serves to decrease the weight of suture loader 510 and facilitates molding of slot 532.

Figure 6:
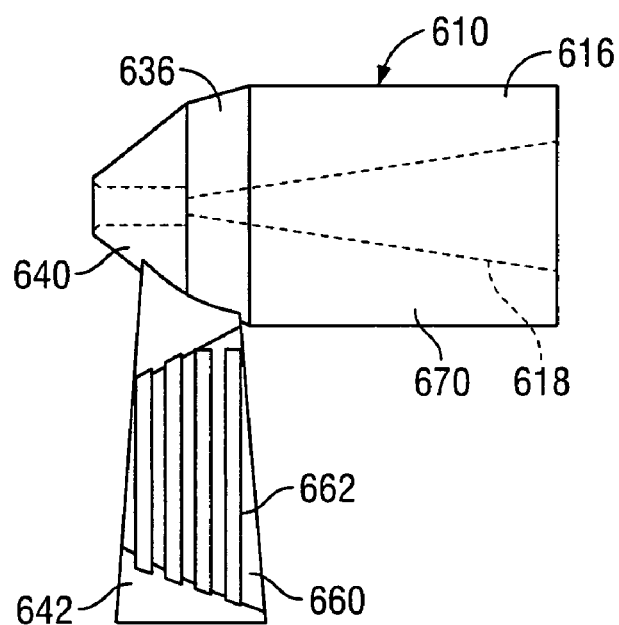
FIG. 6 is a side view of a third embodiment of a suture loader.
Figure 7:
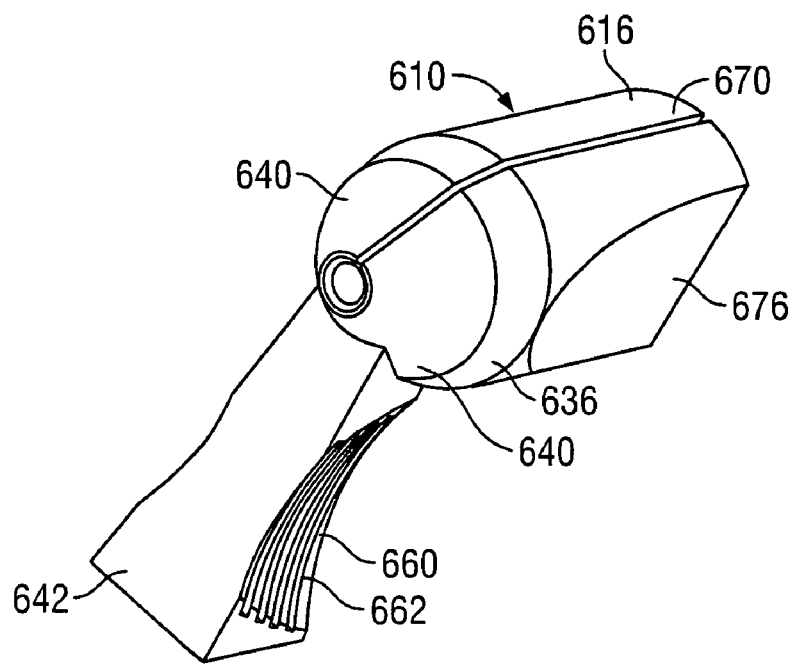
FIG. 7 is a perspective view of the suture loader of FIG. 6.

Referring to FIGS. 6 and 7, a suture loader 610 includes a body 616 having a bottom portion 640, analogous to bottom portion 40, an intermediate portion 636, analogous to portion 36, and an extended portion 670. Body 616 defines a tapered hole 618 that is longer than tapered hole 18 of suture loader 10 to more easily facilitate threading the suture thread into tapered hole 618. Extended portion 670 includes concave cutouts 676 (only one of which is shown) that lighten the weight of suture loader 610 and facilitate grasping body 616. Extending from body 614 is a handle 642 having two recessed sides 660 with ribs 662 that facilitate gripping by the user.

Figure 8:
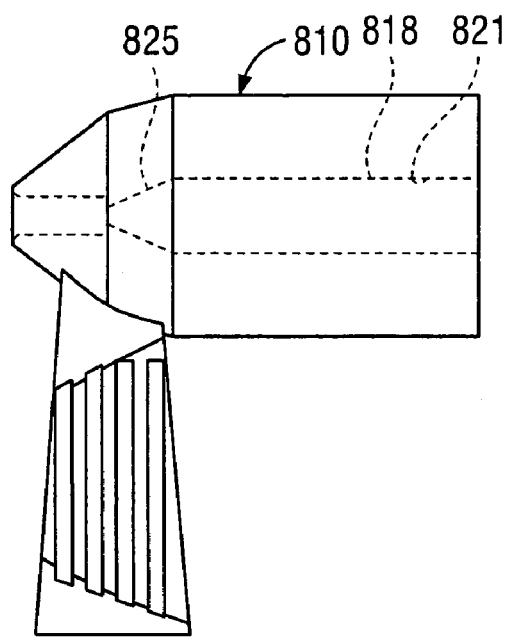
FIG. 8 is a side view of a fourth embodiment of a suture loader.
Figure 9:
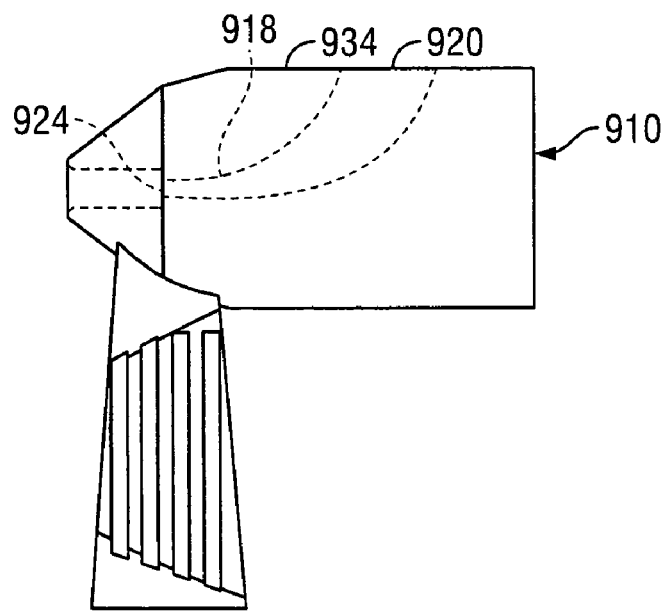
FIG. 9 is a side view of a fifth embodiment of a suture loader.
Figure 10:
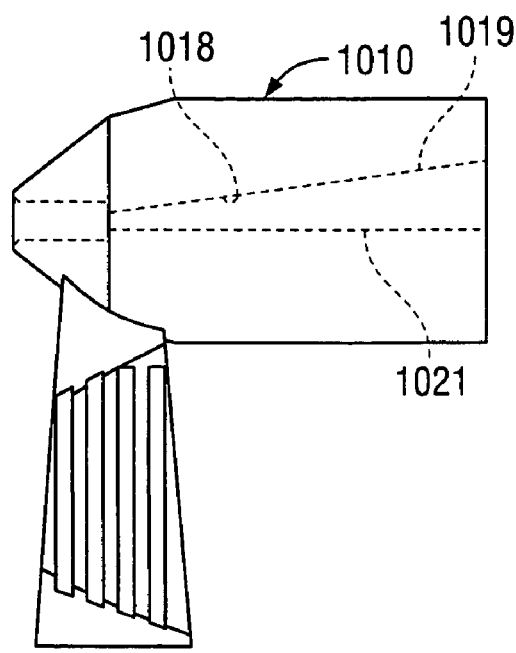
FIG. 10 is a side view of a sixth embodiment of a suture loader.
Figure 11:
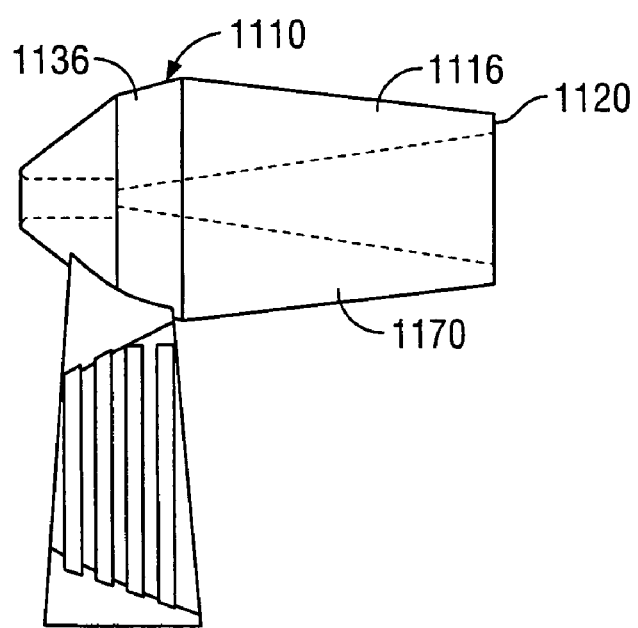
FIG. 11 is a side view of a seventh embodiment of a suture loader.

FIGS. 8-11 show suture loaders 810, 910, 1010, and 1110 having varying shapes and contours of the tapered hole and body. Referring to FIG. 8, a hole 818 includes a constant diameter portion 821 leading to a tapered portion 825. Referring to FIG. 9, a tapered hole 918 curves from an opening 920 in a side surface 934 of suture loader 910 to a smaller diameter opening 924 such that opening 920 is substantially perpendicular to opening 924. Referring to FIG. 10, a tapered hole 1018 is formed by a straight walled portion 1021 and a tapered wall portion 1019. Referring to FIG. 11, an extended portion 1170 of a body 1116 is tapered from a wider diameter at an intermediate portion 1136 to a narrower diameter at a top surface 1120, in order to make suture loader 1110 lighter in weight.

A number of embodiments have been described. Nevertheless, it will be understood that various modifications may be made. For example, the tapered hole can have any suitable shape that facilitates passing a suture into a tube, such as a hole having a square, triangular or other cross section. The slot can be any passage that extends from the tapered hole to the external surface and that allows the suture loader and the suture thread to be separated. Also, the dimensions of the tapered hole, bore, and slot can be varied to accommodate different size suture threads or different size tubes. The body can be made without a handle. The external surface of the body also can have any appropriate shape, such as box-shaped, semi-spherical, or dome-shaped. Also the body can have interstices or cut outs to reduce weight. The suture loader can be made of any suitable material such as stainless steel, plastic, or ceramic. The tube can have any suitable configuration such as being curved, straight, or bent, and being round, elliptical, square, or triangular in cross section. The opening in the tube can, for example, extend the entire length of the tube, through a portion of the tube and may terminate inside the tube or in any of the walls of the tube. While embodiments have been disclosed for loading a suture thread onto a surgical instrument, it will be appreciated that the disclosed embodiments can be used to load any kind of filament onto an instrument that requires the filament to be passed through a narrow passage. These and other embodiments are within the scope of the following claims.

What is claimed is:

1. A device comprising:
    a body having:
        a first portion defining a tapered hole configured for guiding a member into a tube coupled to the body,
        a second portion defining a bore for receiving the tube for passage of the member into the tube from the tapered hole, and
        a projecting surface encircling the bore, the projecting surface being formed on an internal surface of the body at an intersection between the tapered hole and the bore and configured to restrict the tube from passing from the second portion into the first portion,
        the body defining a slot communicating with the hole and the bore for separating the body and the member while the member remains in the tube, the slot extending along the entire length of the body.

2. The device of claim 1 wherein the bore has a constant diameter.

3. The device of claim 1 wherein the bore is tapered.

4. The device of claim 1 wherein the slot extends from the tapered hole and the bore to an external surface of the body.

5. The device of claim 1 further comprising the member and wherein the member comprises a suture thread.

6. The device of claim 1 further comprising a handle extending from the body.

7. The device of claim 1, wherein the body is configured such that the tapered hole guides the member when advanced into the tube from a larger opening of the tapered hole to a smaller opening of the tapered hole.

8. The device of claim 1, wherein the projecting surface defines a circular opening.

9. The device of claim 8, wherein the circular opening has a diameter smaller than the smallest diameter of the bore.

10. A device comprising:
a tube defining a hole through a lateral surface of the tube; and
a body having:
- a first portion defining a tapered hole configured for guiding a member into the tube coupled to the body,
- a second portion defining a bore for receiving the tube for passage of the member into the tube from the tapered hole, and
- a projecting surface formed on an internal surface of the body at an intersection between the tapered hole and the bore and configured to restrict the tube from passing from the second portion into the first portion,
- the body defining a slot communicating with the hole and the bore for separating the body and the member while the member remains in the tube, the slot extending from the tapered hole and the bore to an external surface of the body.

11. The device of claim 10 wherein the body is configured for connection to an end of the tube.

12. The device of claim 10 wherein the bore has a constant diameter.

13. The device of claim 10 wherein the bore is tapered.

14. The device of claim 10 wherein the tube defines an opening for receiving the member.

15. The device of claim 14 wherein a width of the opening is substantially the same as the width of the narrowest portion of the tapered hole.

16. The device of claim 10 further comprising the member and wherein the member comprises a suture thread.

17. The device of claim 10 further comprising a handle extending from the body.

18. The device of claim 10, wherein the slot extends from a terminal end of the first portion to a terminal end of the second portion.

19. The device of claim 10, wherein the body is configured such that the tapered hole guides the member when advanced into the tube from a larger opening of the tapered hole to a smaller opening of the tapered hole.

20. The device of claim 10, wherein the projecting surface is a circumferential projecting surface.

21. The device of claim 10, wherein the tube defines a channel that is curved along a longitudinal extent of the channel.

22. A method comprising:
coupling a body to an end of a tube, the body defining a tapered hole and a slot;
introducing an end of a member into the body through a larger opening of the tapered hole;
after the end of the member is introduced into the body through the larger opening of the tapered hole, guiding the member into the tube through the tapered hole, the tapered hole acting to guide the member when advanced into the tube from the larger opening of the tapered hole to a smaller opening of the tapered hole; and
separating the body and the member by passing the member through the slot, wherein coupling comprises receiving the end of the tube in a bore in the body, the bore communicating with the tapered hole.

23. The method of claim 22, wherein separating the body and the member by passing the member through the slot comprises separating the body and the member by passing the member through the slot while the member remains in the tube.

24. The method of claim 22, further comprising decoupling the body from the end of the tube.

25. A device comprising:
a body having:
- a first terminal end portion defining a tapered hole, and
- a second terminal end portion opposite to the first terminal end portion, the second terminal end portion defining a bore in communication with the tapered hole,
- a projecting surface formed on an internal surface of the body at an intersection between the bore and the tapered hole,
- the body defining a slot extending from the tapered hole and the bore to an external surface of the body and extending from the first terminal end portion to the second terminal end portion; and
a cylindrical handle integrally attached to the body and projecting on only one side of the body opposite to the slot.

26. A device comprising:
a body having:
- a first portion defining a tapered hole configured for guiding a member into a tube coupled to the body,
- a second portion defining a bore for passage of the member therethrough from the tapered hole, the bore having a diameter that is greater than a width of the narrowest portion of the tapered hole, and
- a projecting surface encircling the bore, the projecting surface being formed at an intersection between the first portion and the second portion,
- the body defining a slot communicating with the hole and the bore for separating the body and the member while the member remains in the tube.

27. A device comprising:
a body having:
- a first portion defining a tapered hole configured for guiding a member into a tube coupled to the body,
- a second portion defining a bore for passage of the member therethrough from the tapered hole, the tapered hole and the bore being in communication with each other such that a channel is formed that extends from the first portion to the second portion; and
- a projecting surface encircling the bore, the projecting surface being formed on an internal surface of the body at an intersection between the tapered hole and the bore, the projecting surface projecting from the internal surface of the body to constrict a width of the channel to being less than a width of the bore at the intersection between the tapered hole and the bore,
- the body defining a slot communicating with the hole and the bore for separating the body and the member while the member remains in the tube, the slot extending to an end of the body such that the slot is open at the end.

* * * * *

UNITED STATES PATENT AND TRADEMARK OFFICE
CERTIFICATE OF CORRECTION

PATENT NO. : 7,662,160 B2  Page 1 of 1
APPLICATION NO. : 10/765214
DATED : February 16, 2010
INVENTOR(S) : Raymond Bojarski and George Sikora It is certified that error appears in the above-identified patent and that said Letters Patent is hereby corrected as shown below:

Title page, col. 2, line 2, under Other Publications, delete "02346,malled" and replace with -- 02346, mailed --.

Signed and Sealed this

Fourteenth Day of September, 2010

David J. Kappos
*Director of the United States Patent and Trademark Office*